(12) United States Patent
Santiago

(10) Patent No.: US 8,911,384 B2
(45) Date of Patent: Dec. 16, 2014

(54) WOUND MEASURING DEVICE AND SYSTEM

(76) Inventor: Carmen Celia Santiago, Southlake, TX (US)

( * ) Notice: Subject to any disclaimer, the term of this patent is extended or adjusted under 35 U.S.C. 154(b) by 0 days.

(21) Appl. No.: 13/475,170

(22) Filed: May 18, 2012

(65) Prior Publication Data

US 2012/0302923 A1    Nov. 29, 2012

Related U.S. Application Data

(60) Provisional application No. 61/489,391, filed on May 24, 2011.

(51) Int. Cl.
*A61B 5/103* (2006.01)
*A61B 5/107* (2006.01)
*A61B 5/11* (2006.01)

(52) U.S. Cl.
CPC .............. *A61B 5/1072* (2013.01); *A61B 5/1109* (2013.01)
USPC ............................................ 600/587; 33/512

(58) Field of Classification Search
CPC ..... A61B 5/4528; A61B 5/103; A61B 5/0053
USPC ............ 600/595, 587; 33/430, 465, 472, 473
See application file for complete search history.

(56) References Cited

U.S. PATENT DOCUMENTS

| | | | | | |
|---|---|---|---|---|---|
| 1,065,046 | A | * | 6/1913 | Higgins | 33/472 |
| 1,367,612 | A | * | 2/1921 | McKinney | 33/472 |
| 1,545,424 | A | | 7/1925 | Heimrich | |
| 2,664,768 | A | * | 1/1954 | Clyne | 408/241 R |
| 4,483,075 | A | * | 11/1984 | Kundin | 331/21 |
| 4,525,933 | A | | 7/1985 | Patterson | |
| 4,641,436 | A | * | 2/1987 | Tzen et al. | 33/483 |
| 4,872,268 | A | * | 10/1989 | Perrault | 33/512 |
| 5,131,164 | A | * | 7/1992 | Miller | 33/613 |
| 5,605,165 | A | * | 2/1997 | Sessions et al. | 128/888 |
| 5,745,074 | A | * | 4/1998 | Laude | 701/300 |
| 5,776,082 | A | * | 7/1998 | Riley et al. | 600/594 |
| 6,159,167 | A | * | 12/2000 | Hardin-Naser | 600/587 |
| 6,336,274 | B1 | * | 1/2002 | Ness Webster | 33/474 |
| 6,467,179 | B1 | | 10/2002 | Wolf | |
| 6,886,263 | B2 | * | 5/2005 | Chou | 33/27.02 |
| 7,073,267 | B2 | * | 7/2006 | Butler et al. | 33/203 |
| 7,082,692 | B2 | | 8/2006 | Shapiro | |
| 7,343,688 | B2 | * | 3/2008 | Price | 33/452 |
| 7,464,480 | B2 | * | 12/2008 | Vetromila | 33/436 |
| 8,276,288 | B1 | * | 10/2012 | Yu | 33/512 |
| 2003/0115765 | A1 | * | 6/2003 | Hajla | 33/430 |
| 2006/0283032 | A1 | | 12/2006 | Yang | |
| 2009/0299233 | A1 | * | 12/2009 | Wang et al. | 600/595 |
| 2010/0004564 | A1 | * | 1/2010 | Jendle | 600/587 |
| 2011/0098539 | A1 | * | 4/2011 | Estocado | 600/300 |

FOREIGN PATENT DOCUMENTS

JP       2007225289 A       9/2007

* cited by examiner

*Primary Examiner* — Sean Dougherty
*Assistant Examiner* — Daniel Cerioni
(74) *Attorney, Agent, or Firm* — The Law Firm of Andrea Hence Evans, LLC

(57) ABSTRACT

A wound measuring device and system measures the length, width and depth of a wound. The device and system features first and second ruler members connected and secured by a connecting member which allows the ruler members to move to measure the length and width of a wound. The connecting member affords perpendicular movement of the ruler members providing accurate and consistent measurement of wounds irregular in shape and size. An end of the first or second member is designed to be inserted in the wound to measure the depth and undermining of the wound. Use of the device provides little to no discomfort to the patient.

3 Claims, 4 Drawing Sheets

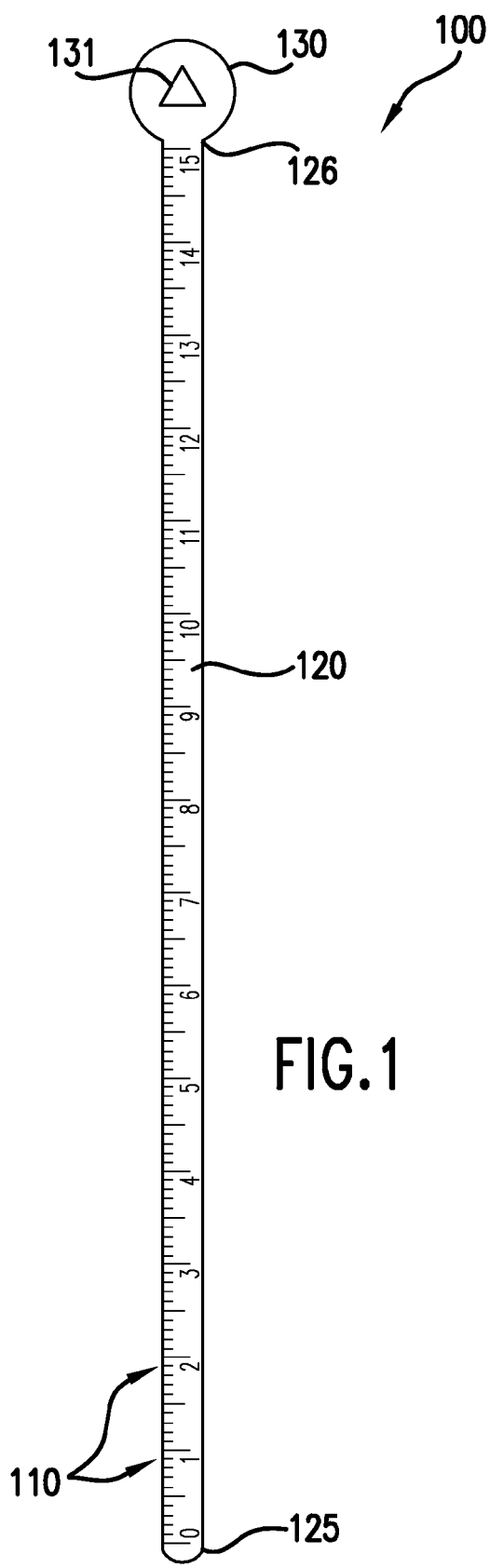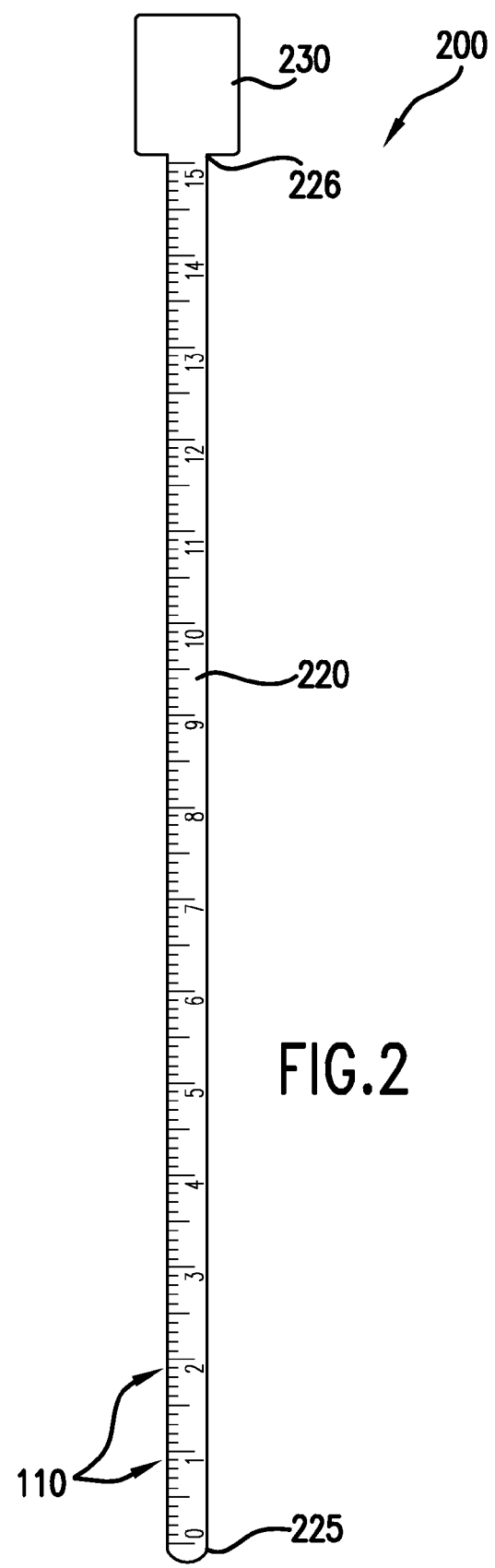

WOUND MEASURING DEVICE AND SYSTEM

RELATED U.S. APPLICATION DATA

This application claims the benefit of provisional application number 61489391, filed May 24, 2011.

FIELD OF THE INVENTION

The present invention relates in general to a device and system to measure wound size and more specifically to a device and system which measures the length, width and depth of a wound.

BACKGROUND OF THE INVENTION

Taking the measurements of a wound allows health care providers to assess the level of tissue damage and to track the healing process. This enables them to determine the appropriate measures to take and to record how well a particular type of wound care is working. Members of the wound care team do not use the same technique to determine the measurements and the results may not be accurate. Measurements are especially unreliable for large or irregular wounds due to inconsistencies in measurements.

SUMMARY OF THE INVENTION

This invention introduces a measuring device and system that measures wound sizes providing a more accurate comparison of measurements and healing or non-healing over time.

An aspect of an embodiment of the invention features the measuring device and system designed for use on curved or flat body surfaces.

A further aspect of an embodiment of the invention features the measuring device and system designed to measure wounds irregular in shape and wounds that cover uneven body surface.

A further aspect of an embodiment of the invention features an accurate, inexpensive and consistent method of measuring wounds.

A further aspect of an embodiment of the invention features ruler members that identify the direction the ruler members should be positioned on the wound.

A further aspect of an embodiment of the invention features ruler members which are secured in a manner which allows perpendicular movement so one member measures the length of the wound and the other member measures the width and either ruler member measures the depth of the wound.

Additional aspects, objectives, features and advantages of the present invention will become apparent from the following description of the preferred embodiments with reference to the attached drawings.

BRIEF DESCRIPTION OF THE DRAWINGS

FIG. 1 is a perspective view of a first ruler member which measures the length of the wound.

FIG. 2 is a perspective member of a second ruler member which measures the width of the wound.

DETAILED DESCRIPTION OF THE INVENTION

Figure 4:
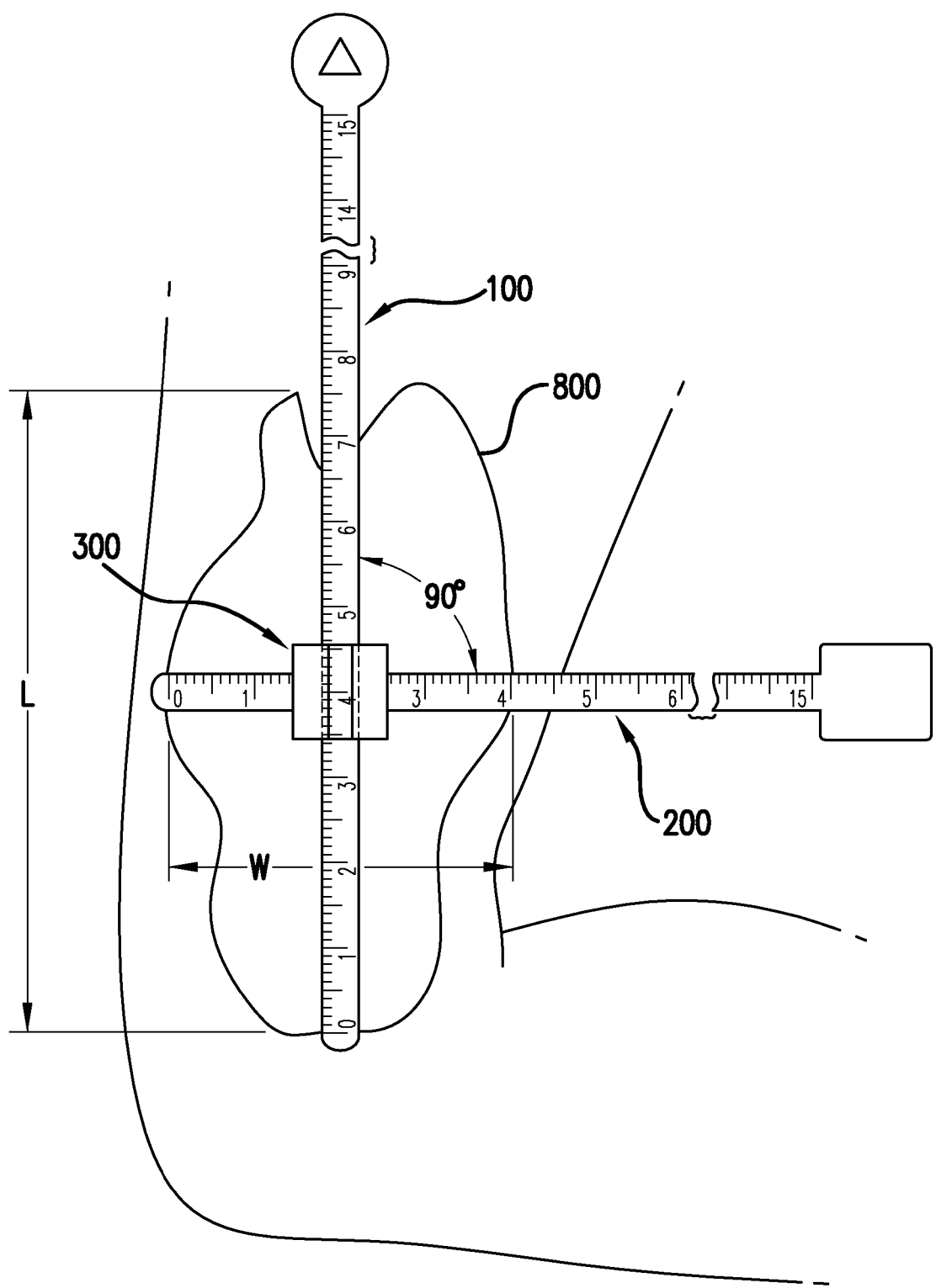
FIG. 4 is a perspective view of the device illustrating the connected first ruler member and second ruler member connected by the connecting device measuring a wound.

FIG. 1 is a perspective view of a first ruler member 100 which measures the length L of the wound 800, as shown in FIG. 4. The first ruler member 100 is a straight strip having measurement indicia 110. The marking indicia 110 are markings along a top surface 120 of the first ruler member 100. The indicia 110 markings are marked at equal intervals along the left or right top edge of the top surface 120 of the first ruler member 100. A bottom end 125 or tip of the first ruler member 100 is marked with a "0" increment marking. A top end 126 of the first ruler member 100 is marked with the largest increment, the length of the measuring area of the first ruler member 100. A direction identifier 130 extends from the top end 126 with a marking or symbol 131 that identifies a direction the first ruler member 100 should be positioned on an object or wound 800 to be measured. The direction identifier may also feature a design or symbol to identify the brand owner or hospital or other identifier which will identify the maker or owner of the tool. The identifier is preferably circular, however, alternate shapes may be used to display the identifier or marking symbol. When the first ruler member 100 is positioned over a wound, 800, it is used to measure the length L of the wound 800. The wound length L is a distance from an end 125 of the first ruler member 100 to a first end of a greatest opening of the wound. The length measurement L is taken when the first ruler member is positioned over the wound or object to be measured.

FIG. 2 is a perspective member of a second ruler member 200 which measures the width W of the wound 800. The second ruler member 200 is a straight strip having measurement indicia 110. The marking indicia 110 are markings along a top surface 220 of the second ruler member 200. The indicia 110 markings are marked at equal intervals along the left or right top edge of the top surface 220 of the second ruler member 200. A bottom end 225 or tip of the second ruler member 200 is marked with a "0" increment marking. A top end 226 of the second ruler member 200 is marked with the largest increment, the length of the measuring area of the second ruler member 200. A handle 230 extends from the top end 226 of the second ruler member 200. The handle 230 allows the user of the second ruler member 200 to manipulate the second ruler member 200 to take measurements. The handle 230 is rectangular in shape, however, an alternate shape may be used. The handle 230 also features an area which receives the wound owner's information such as name, date, etc. A label may be placed on the handle with information or it may be written directly on the handle 230. Measurement indicia are not marked on the direction indicator 130 or the handle 230. When the second ruler member 200 is positioned over a wound or object 800, it is used to measure the width W of the wound 800. Wound width W is a distance from an end of the connected second ruler member 225 to a second end of the greatest opening of the wound.

The tip 125 of the first ruler member 100 or the tip 225 of the second ruler member measures the depth of the object or wound to be measured. The tip 125 of the first ruler member 100 or the tip 225 of the second ruler member 200 is inserted inside of the wound or object its furthest distance inside of the wound or object to a surface of the wound to determine the wound depth.

The first and second ruler members 100, 200 are preferably light grey or transparent in color. When placed over the wound 800 or object, the light color or transparency affords the measurements to easily and accurately be taken and seen as well as it affords the measurer the ability to see the wound 800 or object to be measured underneath the rulers, 100, 200. Additional light colors may be used so long as they do not obstruct the view of the measurer or conceal the object to be measured. The markings 110 are preferably in a black or other color that can easily be seen so that an accurate measurement may be identified. Markings 110 shown in FIGS. 1 and 2 are in centimeters. Ruler members 100, 200 provide measurements up to 15 cm in width and 15 centimeters in length. The markings may be shown in alternate metric units and the measurements may be increased or decreased to measure larger or shorter objects. The ruler members 100, 200 are flexible so they can be placed on curved body surfaces as well as flat body surfaces to accurately measure. Furthermore, the ruler members 100, 200 can easily be maneuvered over irregular sized objects to be measured. The rulers are sterilized for a one-time use. It is recommended for sanitary purposes that the rulers not be reused to avoid infections, for example. Open packages and unused ruler members should be discarded.

Figure 3A:
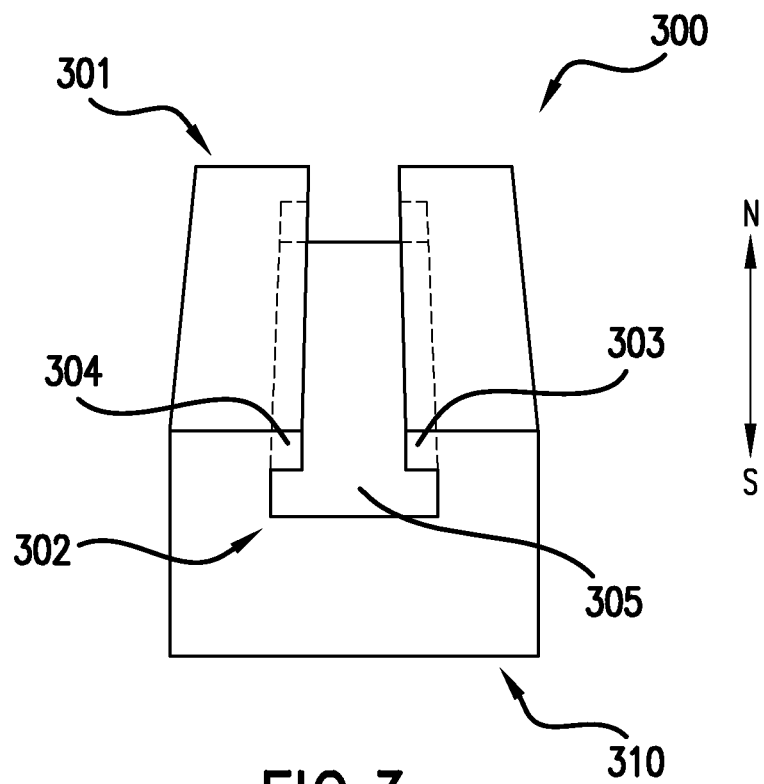
FIG. 3a is a top side of a perspective view of a connecting device which secures and connects the first ruler member and second ruler member.

FIG. 3a is a top side 301 of a perspective view of a connecting device 300 which secures and connects the first ruler member 100 and second ruler member 200. The connection device 300 allows perpendicular movement of the first ruler member 100 and second ruler members 200 so that the rulers move in a sliding motion independent of each other. The connecting device 300 top side 301 features a first connector 302. The first connector 302 features parallel first connector flanges 303, 304. The flanges 303, 304 form a first channel 305 sized to receive the first ruler member 100. The flanges' 303, 304 walls contact the left and right outermost edges of the first ruler members so that the first ruler member remains secure in the connector 302. The first ruler member 100 can movely back and forth or in and out freely through the channel. The connecting device is also a light grey or transparent color so that the markings on the ruler members remain visible. The channel has a bottom that receives and contacts a bottom side of the ruler member 100. However, the area between the flanges 303, 304 remains open so the markings can easily be identified and measurements can be recorded.

Figure 3B:
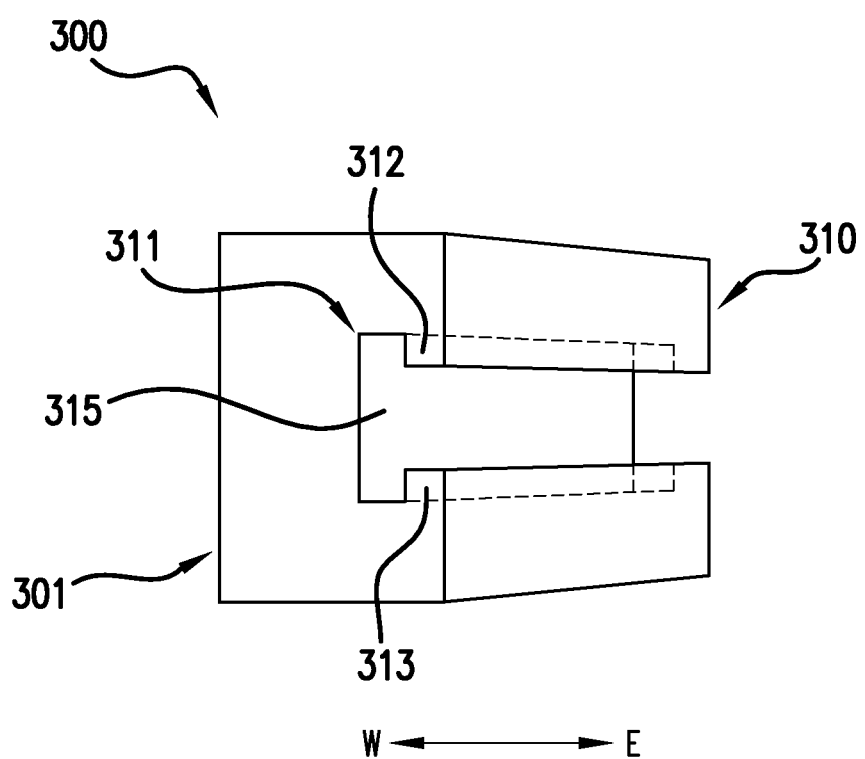
FIG. 3b is a bottom side of a perspective view of a connecting device which secures and connects the first ruler member and second ruler member.
Figure 5:
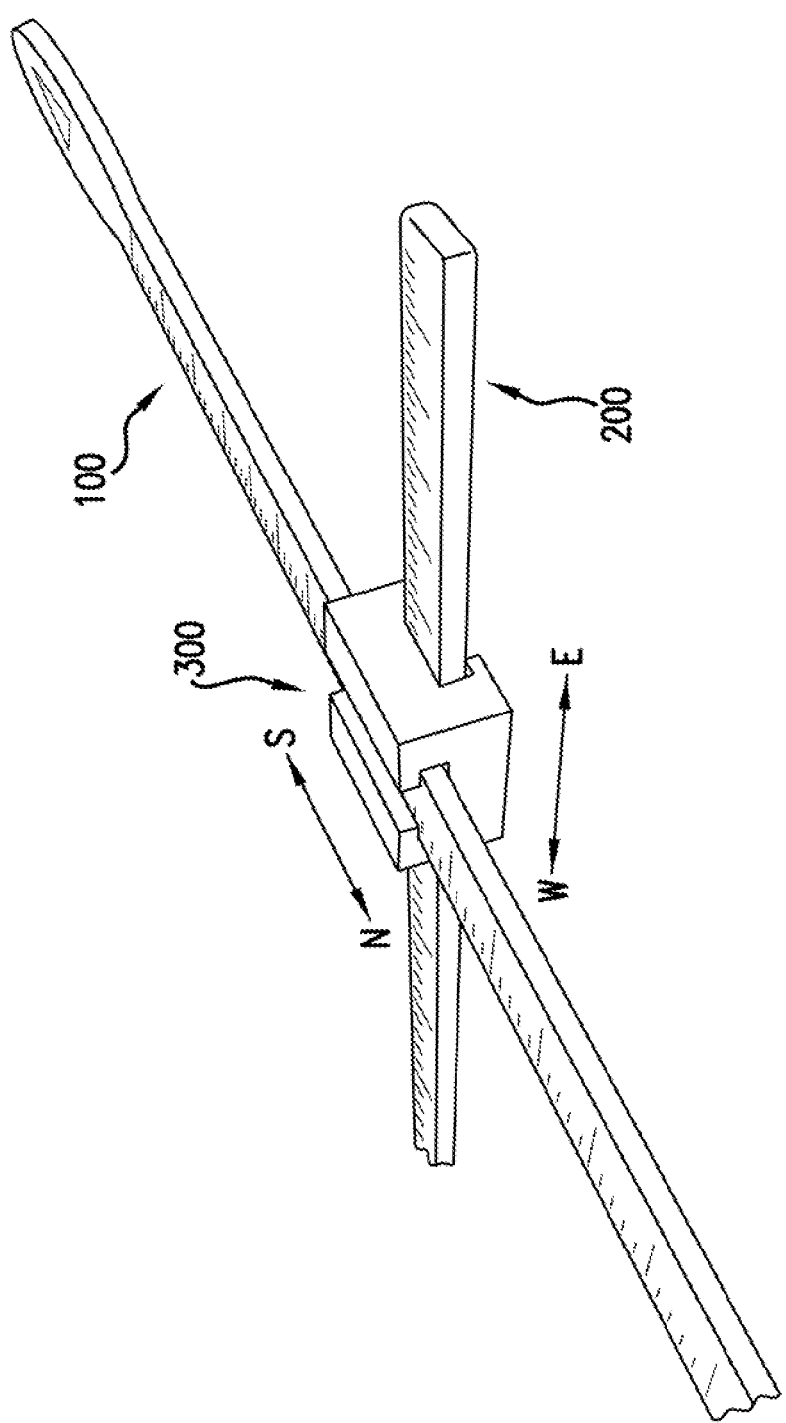
FIG. 5 is a perspective view of the device illustrating the connected first ruler member and second ruler member connected by the connecting device.

FIG. 3b is a bottom side 310 of a perspective view of the connecting device 300 which secures and connects the first ruler member 100 and second ruler member 200. The bottom side 310 of the connecting device 300 is a second connector 311 having second connector parallel flanges 312, 313 that form a second channel 315 sized to receive the second ruler member 200. The flanges 312,313 walls contacts the left and right outermost edges of the second ruler members so that the second ruler member remains secure in the connector 310. The second ruler member 200 can movely back and forth or in and out freely through the channel 315. The channel 315 has a bottom that receives and contacts a bottom side of the ruler member 200. However, the area between the flanges 312, 313 remains open so the markings can easily be identified and measurements can be recorded. The first connector 301 and second connector 310 are attached so that the first connector's bottom side is secured to the second connector's bottom side. However, the first connector 301 is secured so that its channel 305 receives the first ruler member in a North to South direction so that the first ruler member 100 moves through the channel 305 in an up and down direction, as shown in FIG. 5. The second connector 310 is secured to the first connector so that its channel 315 receives the second ruler member in a East to West direction so that the second ruler member 200 moves through the channel 315 in a left to right direction, as shown in FIG. 5. The connecting device affords the first ruler member and second ruler member the ability to move independently of each other so that when the connecting device secures the first and second ruler members, there is always a perpendicular angle between the first and second rulers.

FIG. 4 is a perspective view of the device illustrating the connected first ruler 100 member and second ruler member 200 connected by the connecting device 300 measuring a wound 800 on a body part such as a leg, for example. The connected ruler members form a measuring tool which may be used to measure the length, width and depth of a wound. The direction identifier 130 on the first ruler member identifies a direction the first ruler member 100 should be positioned on the wound 800 to be measured. The identifier is preferably an arrow, but another symbol may be used to identify which direction the ruler 100 should be positioned. The arrow should point to the wound owner's head, when the first ruler member 100 is placed over the wound opening. While keeping the arrow pointed towards the wound owner's head, the first ruler member 100 is adjusted so it measures the greatest expanse or opening of the wound from that direction. This is the wound length L. Without moving the first ruler member 100, the second ruler member 200 is slide through the connecting device 300 so it measures the wound expanse or opening at the point where the greatest expanse or opening can be recorded. This is the wound width W. When connected, the first and second members, 100, 200 move perpendicular to each other. The wound length L and wound width W are recorded. Also, a time-marked camera may be used to take pictures of the placement and thus the measurements of the wound. Using the first ruler member tip 125 or second ruler member tip 225 where the indicator starts with "0" cm, the width depth and undermining is recorded as described above.

The use of the measuring tool is contraindicated for use in measuring burns, rash or other abrasions not resulting in a puncture, cut, scrape or tear. Also, the tool is contraindicated for use in measuring surgical incisions other than those experiencing dehiscence.

The invention has been described in detail with particular reference to certain preferred embodiments thereof, but it will be understood that variations and modifications can be effected within the spirit and scope of the invention.

The invention claimed is:

1. A method of measuring a wound having a first and second wound opening with a wound length, wound width and wound depth comprising:
   providing a measuring tool having a first ruler member and a second ruler member;
   wherein measurement indicia is on a top surface of the first ruler member and the second ruler member;
   positioning the first ruler member over the wound opening;
   measuring the wound length with the first ruler, wherein the wound length is a distance from an end of the first ruler member at the first wound opening to a first end of a greatest opening of the wound;
   providing a connecting member that connects the first ruler member and the second ruler member, so that the first and second member move perpendicular to each other;
   wherein the connecting member features a first connector having a first channel formed between first connector flanges, wherein the first channel receives the first ruler member and a second connector having a second channel formed between second connector flanges, wherein the second channel receives the second ruler member, wherein the connecting member further comprises a first aperture that extends from a top side of the first channel to a first side of the connecting member and a second aperture extending from a top side of the second channel to a second side of the connecting member, the first side of the connecting member being opposite the second side of the connecting member;

wherein the top side of the first channel and the top side of the second channel are proximate to the top surface of the first ruler member and the second ruler member, respectively;

connecting the second ruler member to the first ruler member;

measuring the wound width with the second ruler member, wherein the wound width is a distance from an end of the second ruler member at the second wound opening to a second end of the greatest opening of the wound;

wherein the first and second apertures are configured to permit visibility of the measuring indicia.

2. The method of claim 1 further comprising measuring the width depth with a first ruler member tip or second ruler member tip, wherein the width depth is a distance from the tip of the first or second ruler member placed its furthest distance inside of the wound to a surface of the wound.

3. The method of claim 1 further comprising providing a direction identifier on an end of the first ruler member that identifies a direction the first ruler member should be positioned on the wound to be measured.

* * * * *